United States Patent [19]

Hyatt et al.

[11] Patent Number: 5,360,723
[45] Date of Patent: Nov. 1, 1994

[54] METHOD FOR LOWERING MOLECULAR WEIGHT OF MICROBIAL CELLULOSES

[75] Inventors: John A. Hyatt, Kingsport; Robert M. Gardner, Gray; Scott R. Thatcher, Johnson City, all of Tenn.

[73] Assignee: Eastman Chemical Company, Kingsport, Tenn.

[21] Appl. No.: 57,922

[22] Filed: May 7, 1993

[51] Int. Cl.$^5$ .............................. C21P 19/04
[52] U.S. Cl. ................. 435/101; 435/822; 435/823
[58] Field of Search ............ 435/101, 823, 822

[56] References Cited

U.S. PATENT DOCUMENTS 4,788,146  11/1988  Ring et al. ............................ 435/101
4,942,128  7/1990   Brown, Jr. ............................ 435/101

OTHER PUBLICATIONS

Gale et al., "J. Gen. Microbiol", (1984), 130, pp. 3303–3311 (see Fx. p. 3305, Mixture Glucose + 2DG + Microorg).

J. Kennedy et al., eds., "Wood and Cellulosics: Industrial Utilization, Biotechnology, Structure, and Properties", Halsted Press, New York, 1987.

S. Yamanaka, "Production and Application of Bacterial Cellulose", Cellulosics Utilization: Research and Rewards in Cellulosics, ed. Inagaki et al., Elsevier Applied Science.

D. White and M. Brown, Jr., "Prospects for the Commercialization of the Biosynthesis of Microbial Cellulose", C. Sucherch, ed., Cellulose and Wood Chemistry and Technology, Wiley, N.Y.

R. Brown, Jr., "Bacterial Cellulose", in J. Kennedy et al., eds., Cellulose: Structural and Functional Aspects, Halsted Press, New York, 1989.

P. Doty et al., "Cellulose and Cellulose Derivatives", ed. E. Ott et al., Interscience, New York, pp. 1133 ff., 1955.

Critical Reviews in Microbiology, vol. 17, p. 436, 1991.

S. Kuga et al., in J. Kennedy et al., eds., "Cellulose: Structural and Functional Aspects", Halsted Press, New York, 1989.

Haigler et al., Science, 210, p. 903 (1980).

Ogawa et al., Carbohydrate Polymers 19, p. 171 (1992).

*Primary Examiner*—Herbert J. Lilling
*Attorney, Agent, or Firm*—Bernard J. Graves, Jr.

[57] ABSTRACT

Provided is a method for controlling the molecular weight (i.e., lowering) of microbially-derived celluloses. The lowering of the molecular weight is achieved by adding 2-deoxy-D-glucose to the liquid or solid medium in which *Acetobacter xylinum* or any other cellulose-producing microbe is grown. The molecular weight of the cellulose produced by the microbes grown in such media varies approximately inversely with the concentration of 2-deoxy-D-glucose in the culture medium. The method thus provided by the present invention is useful in providing microbial source cellulose which has a number average molecular weight of about $7 \times 10^5$ to about $1 \times 10^4$. Such lower molecular weight celluloses are useful in coatings formulations in which a relatively lower viscosity binder is desired.

7 Claims, 1 Drawing Sheet

METHOD FOR LOWERING MOLECULAR WEIGHT OF MICROBIAL CELLULOSES

FIELD OF THE INVENTION

This invention belongs to the field of cellulose chemistry. In particular, it relates to a method for controlling the molecular weight, i.e., lowering the molecular weight of celluloses prepared by cellulose producing microorganisms.

BACKGROUND OF THE INVENTION

Cellulose is one of the most widely utilized polymeric materials. Both unmodified ("native") and chemically modified or derivatized celluloses are of great commercial importance in areas such as textiles, food additives, coatings, filter media, packaging, and medical devices. A recent review of cellulose production and utilization is given in J. Kennedy, G. Phillips, and P. Williams, eds., "Wood and Cellulosics: Industrial Utilization, Biotechnology, Structure, and Properties," Halsted Press, New York, 1987.

Cellulose is obtained principally from the cell wall tissues of higher plants such as cotton, flax, ramie, and both hardwood and softwood trees. It has in recent years become possible, however, to obtain pure celluloses produced by various microbial organisms. Several articles and patents address the special properties and utility of cellulose obtained from microbes:

- S. Tamanaka, "Production and Application of Bacterial Cellulose," in *Cellulosics Utilization: Research and Rewards in Cellulosics,* ed. Inagaki and Phillips, Elsevier Applied Science, 1989.
- D. White and M. Brown, Jr., "Prospects for the Commercialization of the Biosynthesis of Microbial Cellulose," in C. Sucherch, ed., *Cellulose and Wood Chemistry and Technology,* Wiley, New York, 1989.
- D. Ring, W. Nashed, and T. Dow, U.S. Pat. No. 4,788,146 (1988), "Liquid Loaded Pad for Medical Applications."
- R. Brown, Jr., "Bacterial Cellulose," in J. Kennedy, G. Phillips, and P. Williams, eds., *Cellulose: Structural and Functional Aspects,* Halsted Press, New York, 1989.
- R. Brown, Jr., U.S. Pat. No. 4,942,128 (1990), "Microbial Cellulose Modified During Synthesis", incorporated herein by reference.

In the field of utilization of celluloses, it is well known that the molecular weight of the cellulose or cellulose derivative is of crucial importance in controlling the physical properties of the polymer. There is often a desirable gain in ease of formulation, application, or preparation of cellulose derivatives with a decrease in the molecular weight of the starting cellulose which correlates to a lower viscosity for the resulting cellulose derivative. This is discussed by P. Doty and H. Spurlin on pp 1133 ff. in *Cellulose and Cellulose Derivatives,* ed. E. Ott, H. Spurlin, and M. Grafflin, Interscience, New York, 1955. Thus, there is a need for producing cellulose with lower molecular weight.

It is known that cellulose can be produced through culture of organisms in the genera Acetobacter, Agrobacterium, Rhizobium, Pseudomonas, and Sarcina. Details of the specific organisms are given in *Critical Reviews in Microbiology,* Vol. 17, p 436 (1991). Furthermore, certain algal species such as Valonia are known to produce harvestable cellulose.

The most frequently studied bacterial cellulose-producer is *Acetobacter xylinum.* Articles by Yamanaka, by Brown, Jr., and by White and Brown, Jr., cited above provide reviews of the current status of Acetobacter cellulose production and utilization. Further, S. Kuga, N. Mutoh, A. Isogai, M. Usuda, and R. Brown, Jr. in J. Kennedy, G. Phillips, and P. Williams, eds., *Cellulose: Structural and Functional Aspects,* Halsted Press, New York, 1989, discuss the determination of the molecular weight of microbial celluloses.

While many workers have reported production and utilization of Acetobacter cellulose, none have reported the existence of a method for the control of the molecular weight of the cellulose produced by the organism. U.S. Pat. No. 4,942,128 teaches that the cellulose produced by Acetobacter grown in a medium containing the additive carboxymethylcellulose possesses an elastic, resilient texture not seen in normal Acetobacter cellulose. Further, Haigler, Brown, Jr., and Benziman report (*Science* 210, 903 (1980)) that the fluorescent brightener CALCOFLUOUR White ST, when added to an *Acetobacter xylinum* culture, leads to the production of a cellulose pellicle of modified crystallinity. But these reports all deal with the formation of a cellulose having modified morphology or solid-state properties; none teach the use of culture medium additives to control the molecular weight of bacterial cellulose.

Finally, Ogawa and Tokura (*Carbohydrate Polymers* 19, 171 (1992)) report that when grown in a medium containing N-acetylglucosamine, *Acetobacter xylinum* produced a cellulose pellicle containing from 0.5–4.0 mole % N-acetylglucosamine incorporated into the cellulose chain. They do not report or discuss the molecular weight of the polymer produced by this procedure.

The present invention as described below, provides a novel method for producing microbial celluloses having molecular weights different from that of normal, "unmodified" microbial celluloses.

SUMMARY OF THE INVENTION

Figure 1:
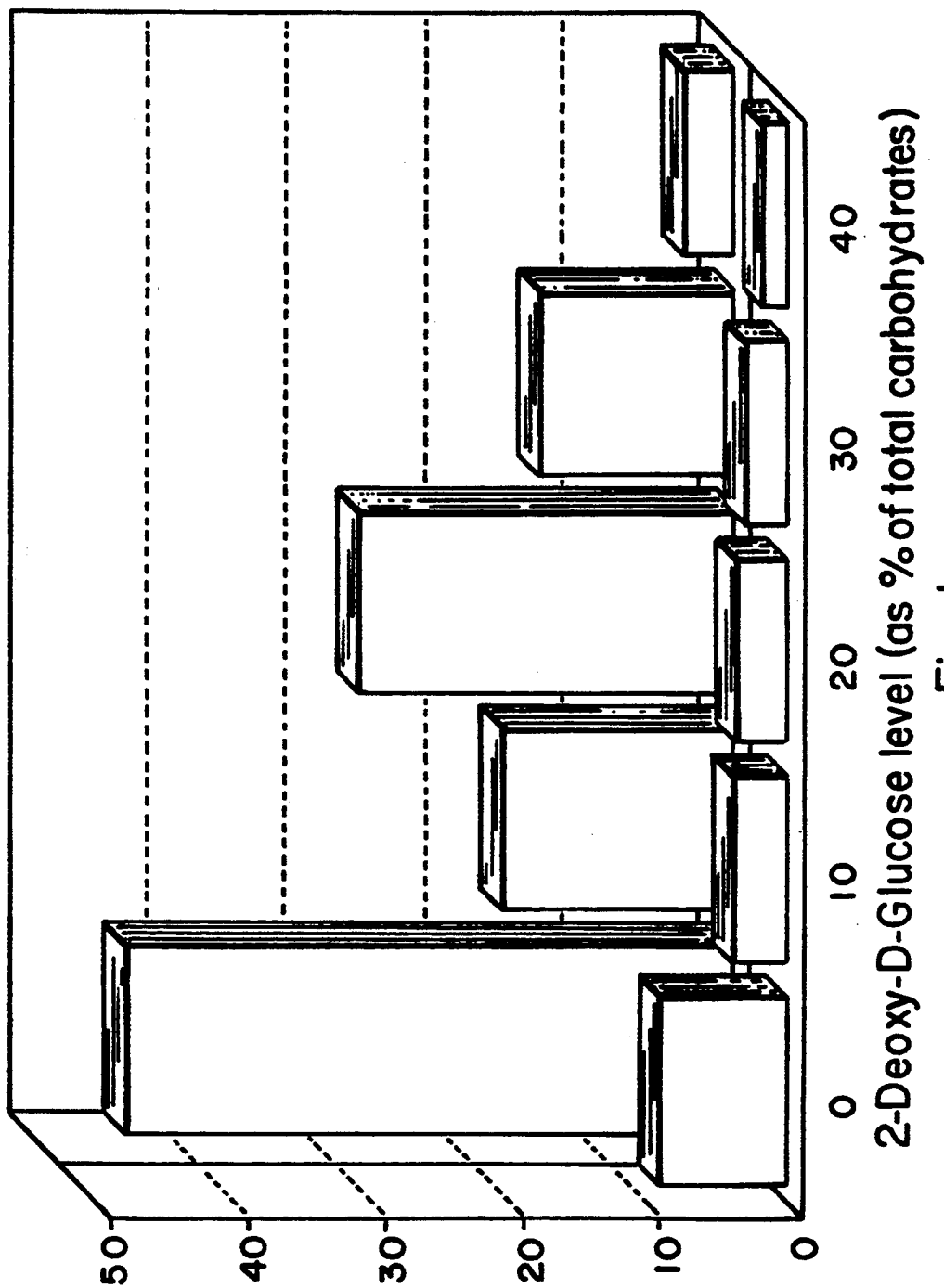
FIG. 1 is a plot of molecular weight ($\times 10^5$) (vertical axis) versus 2-deoxy-D-glucose level (as weight % of total carbohydrates). The number average molecular weight is in the foreground and the weight average molecular weight is in the background.

The present invention provides a method for controlling the molecular weight (i.e., lowering the molecular weight) of microbially-derived celluloses. The lowering of the molecular weight is achieved by adding 2-deoxy-D-glucose to the liquid or solid medium in which *Acetobacter xylinum* or any other cellulose-producing microbe is grown. The molecular weight of the cellulose produced by the microbes grown in such media varies approximately inversely with the concentration of 2-deoxy-D-glucose in the culture medium. The method thus provided by the present invention is useful in providing microbial source cellulose which has a number average molecular weight of about $7 \times 10^5$ to about $1 \times 10^4$. Such lower molecular weight celluloses are useful in coatings formulations in which a relatively lower viscosity binder is desired.

DETAILED DESCRIPTION OF THE INVENTION

The invention comprises the addition of the compound 2-deoxy-D-glucose to the liquid or solid medium in which *Acetobacter xylinum* or other cellulose-producing microbe is grown. The molecular weight of the cellulose produced by the microbes grown in such media varies approximately inversely with the concentration of 2-deoxy-D-glucose in the culture medium.

Thus, when about 30% of the D-glucose in the culture medium was replaced by 2-deoxy-D-glucose, the weight-average molecular weight of *Acetobacter xylinum* cellulose produced was about half that of the cellulose produced in a "normal" medium (100% D-glucose).

The reduced molecular weight polymer produced in the presence of 2-deoxy-D-glucose was found to contain up to 2.5 mole % of 2-deoxy-D-glucose.

In the practice of the present invention, any strain of cellulose-producing microorganism species can be employed. Thus *Acetobacter xylinum* strains ATCC 10821 or others may be used, as can any cellulose-producing strains of such species as *Acetobacter aceti* AJ 12368, *Sarcini ventriculi*, *Agrobacter tumefaciens*, and the like. *Acetobacter xylinum* ATCC 10821 cultures may be obtained from the American Type Culture Collection (ATCC), Rockville, Md. (see ATCC Catalogue of Bacteria & Bacteriophages, Eds., R. Gherma, P. Pienta, and R. Cote, 17th Ed., 1989). This species is also available from the National Collection of Type Cultures (NCTC), London, England, and the National Collection of Industrial Bacteria (NCIB), Aberdeen, Scotland. The strain number for both the NCTC and the NCIB is 1375.

Any growth medium which supports the growth of the organism and allows production of a cellulosic pellicle may be employed. The level of 2-deoxy-D-glucose in the medium can range from about 5% to about 95% of the total carbohydrates present.

The polymer produced by the organisms under these conditions can be entirely β-1,4-D-glucan (conventional cellulose) or may be β-1,4-D-glucan containing up to 5 mole % of 2-deoxy-D-glucose as internal or end group substitutions for D-glucose.

Thus, the present invention provides a method for preparing β-1,4-glucan or β-1,4-D-glucan containing up to 5 mole % of 2-deoxy-D-glucose as internal or end group substitutions for D-glucose, which comprises culturing a cellulose-producing microorganism under aerobic fermentation conditions in the presence of assimilable sources of carbon, hydrogen, and nitrogen, said sources comprised of D-glucose and 2-deoxy-D-glucose.

In a preferred embodiment of the invention, there is provided a method for preparing β-1,4-D-glucan or β-1,4-D-glucan containing up to 5 mole % of 2-deoxy-D-glucose as internal or end group substitutions for D-glucose, wherein said β-1,4-d-glucan or β-1,4-D-glucan containing up to 5 mole % of 2-deoxy-D-glucose as internal or end group substitutions for D-glucose has a molecular weight of about $7 \times 10^5$ to about $1 \times 10^4$, which comprises culturing a cellulose-producing microorganism under aerobic fermentation conditions in the presence of assimilable sources of carbon, hydrogen, and nitrogen, said sources comprised of a mixture of D-glucose and 2-deoxy-D-glucose in a weight/weight ratio of about 9/1 to about 1/2.5.

In the above process, the aerobic fermentation conditions are conventional; thus, a temperature at the so-called optimal temperature of 30° C. plus or minus 5° C. is preferred. In the growth media, a concentration of about 1.5% of carbohydrates is preferred.

EXPERIMENTAL SECTION

*Acetobacter xylinum* Cultures: Cultures of *Acetobacter xylinum* strain 10821 were purchased from the American Type Culture Collection (Rockville, Md.). Lyophilized cultures (freeze-dried) were reactivated by suspension into Mannitol Broth and incubated at 30° C. under static conditions. Manitol Broth contained the following ingredients on a per liter basis: 5.0 g Yeast Extract (DIFCO Laboratories), 3.0 g PEPTONE (BBL Microbiology Systems), and 25.0 g D-mannitol (Sigma Chemical Company). This medium was dispensed in 15 mL aliquots, placed in sterile test tubes, and sealed with Morton Closures. The Mannitol Broth was then sterilized by autoclaving at 121° C. for 15 minutes at 15 psi. After incubation, the cellulose pellicle was aseptically harvested and placed in 10 mLs of sterile phosphate buffered saline (PBS), which had the following formulation: 20 mM $K_2HPO_4$ and 0.85% (wt./vol.) NaCl, adjusted to pH 7.0. The pellicle was washed three times in 10 mL of PBS. The cellulose pellicle was then macerated to release the cellulose forming bacteria. A sterile inoculating loop was then used to streak for isolation on a Mannitol Agar plate. This medium had the same formulation as that for the Mannitol Broth, with the exception that it had an additional 1.5% (wt./vol.) agar (DIFCO). Plates were incubated at 30° C. for two days or until the appearance of isolated colonies. Isolated colonies were aseptically picked and transferred back into Mannitol Broth and placed at 30° C. These cultures became the working stock cultures for this invention and were transferred once a month to insure viability.

Growth Media

The basal growth medium was modified for all experimentation involving 2-deoxyglucose. The following formulation was employed: 0.5% (wt/vol) Difco yeast extract, 0.3% (wt/vol) BBL peptone, and 1.5% (wt/vol) total carbohydrates which included differing ratios of D-glucose and 2-deoxyglucose. The following ratios were evaluated: 90% glucose/10% 2-deoxyglucose, 80% glucose/20% 2-deoxyglucose, 70% glucose/30% 2-deoxyglucose, 60% glucose/40% 2-deoxyglucose, and 50% glucose/50% 2-deoxyglucose. This medium was dispensed into 200 mL aliquots and sterilized at 121° C., 15 psi, for 30 mins.

Inoculum Preparation

The inoculum was obtained by harvesting the cellulose pellicle out of the stock cultures. A 1 cm square was then aseptically removed from this piece and washed thoroughly in 20 mM $K_2HPO_4$ buffer with 0.85% wt/vol NaCl. The washing action served to remove non-cellulose producing *Acetobacter xylinum* strains. The washed cellulose pellicle was then placed in a sterile petri dish and finely divided with a surgical scalpel into pieces of approximately 0.5 mm square. The small cellulose pieces were then resuspended in 10 mL of buffered saline and taken up in a sterile pipet. To each new culture 0.1 mL was transferred, thus insuring several small pieces of cellulose were added to each flask. Subsequent work with 2-deoxyglucose has shown that repeated transfers in media containing 70% glucose/30% 2-deoxyglucose greatly reduces the lag time before the initiation of new cellulose production. Thus, with the exception of the first experiment, all other work utilized inocula that were previously adapted to 2-deoxyglucose. All cultures were incubated at 30° C. under static conditions.

Procedure for Recovery of Cellulosic Products

The pellicles harvested from the *Acetobacter xylinum* cultures which had been inoculated and grown as described above were cleaned by boiling for 1-2 hours in a detergent solution of the composition described by Goering and Van Soest, "Forage Fiber Analyses," Agriculture Handbook No. 379, U.S. Dept. of Agriculture, pp 5-6. The detergent solution comprised 90 grams of sodium lauryl sulfate, 30 mL of ethylene glycol monoethyl ether, 20.4 grams of sodium borate, and 13.7 grams of dibasic sodium phosphate, diluted to 3 liters with sterile water.

The boiled, transparent pellicles were then washed with 2-3 liters of boiling water, with 200 mL of glacial acetic acid, stored overnight in glacial acetic acid, and re-washed with copious amounts of distilled water. The polymer pellicles were then subjected to acetylation in trifluoroacetic anhydride-acetyl chloride and the resulting cellulose triacetates analyzed by gel permeation chromatography. The number- and weight-average molecular weights obtained from pellicles grown in media containing different levels of 2-deoxy-D-glucose are illustrated in FIG. 1.

We claim:

1. A method for preparing $\beta$-1,4-D-glucan or $\beta$-1,4-D-glucan containing up to 5 mole % of 2-deoxy-D-glucose as internal or end group substitutions for D-glucose, which comprises culturing a cellulose-producing microorganism, wherein the cellulose-producing microorganism is selected from *Acetobacter xylinum, Acetobacter aceti, Sarcini ventriculi,* and *Agrobacter tumefaciens,* under aerobic fermentation conditions in the presence of assimilable sources of carbon, hydrogen, and nitrogen, said sources comprised of D-glucose and 2-deoxy-D-glucose.

2. The method of claim 1, wherein the cellulose-producing microorganism is *Acetobacter xylinum*.

3. The method of claim 1, wherein the cellulose-producing microorganism is *Acetobacter xylinum* ATCC 10821, or a chemically-induced mutation thereof.

4. A method for preparing ($\beta$-1,4-D-glucan or $\beta$-1,4-D-glucan containing up to 5 mole % of 2-deoxy-D-glucose) as internal or end group substitutions for D-glucose, wherein said $\beta$-1,4-D-glucan or $\beta$-1,4-D-glucan containing up to 5 mole % of 2-deoxy-D-glucose as internal or end group substitutions for D-glucose has a number average molecular weight, as determined by gel permeation chromatography, of about $7 \times 10^5$ to about $1 \times 10^4$, which comprises culturing a cellulose-producing microorganism, wherein the cellulose-producing microorganism is selected from *Acetobacter xylinum, Acetobacter aceti, Sarcini ventriculi,* and *Agrobacter tumefaciens,* under aerobic fermentation conditions in the presence of assimilable sources of carbon, hydrogen, and nitrogen, said sources comprised of a mixture of D-glucose and 2-deoxy-D-glucose.

5. The method of claim 4, wherein the D-glucose and 2-deoxy-D-glucose are present in a weight/weight ratio of about 9/1 to about 1/2.5.

6. The method of claim 4, wherein the cellulose-producing microorganism is *Acetobacter xylinum*.

7. The method of claim 4, wherein the cellulose-producing microorganism is *Acetobacter xylinum* ATCC 10821, or a chemically-induced mutation thereof.

* * * * *

UNITED STATES PATENT AND TRADEMARK OFFICE
CERTIFICATE OF CORRECTION

PATENT NO. : 5,360,723

DATED : November 1, 1994

INVENTOR(S) : John A. Hyatt et al

It is certified that error appears in the above-identified patent and that said Letters Patent is hereby corrected as shown below:

Column 6, line 4 (Claim 1, line 11), after "2-deoxy-D-glucose", please add --- and recovering said β-1,4-D-glucan or β-1,4-D-glucan containing up to 5 mole % of 2-deoxy-D-glucose ---.

Column 6, line 26 (Claim 4, line 16), after "2-deoxy-D-glucose", please add --- and recovering said β-1,4-D-glucan or β-1,4-D-glucan containing up to 5 mole % of 2-deoxy-D-glucose ---.

Signed and Sealed this

Second Day of May, 1995

Attest:

BRUCE LEHMAN

Attesting Officer     Commissioner of Patents and Trademarks